(12) United States Patent
Bryant et al.

(10) Patent No.: US 6,355,638 B1
(45) Date of Patent: Mar. 12, 2002

(54) PYRAZOLO[1,5-D][1,2,4] TRIAZINES FOR ENHANCING COGNITION

(75) Inventors: Helen Jane Bryant, Roydon; William Robert Carling, Bishops Stortford; Mark Stuart Chambers, Puckeridge; Sarah Christine Hobbs, Great Dunmow; Philip Jones; Angus Murray MacLeod, both of Bishops Stortford, all of (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/717,423

(22) Filed: Nov. 21, 2000

(30) Foreign Application Priority Data

Nov. 25, 1999 (GB) ............................................. 9927874
Apr. 18, 2000 (GB) ............................................. 0009602
Jul. 28, 2000 (GB) ............................................. 0018651

(51) Int. Cl.$^7$ ...................... C07D 487/14; A61K 31/53; A61P 25/28
(52) U.S. Cl. ....................................... 514/243; 544/184
(58) Field of Search .......................... 544/184; 514/243

(56) References Cited

PUBLICATIONS

R.K. McNamara et al., *Psychobiology*, 21:101–108(1993).

*Primary Examiner*—Mukund J. Shah
*Assistant Examiner*—Venkataraman Balasubramanian
(74) *Attorney, Agent, or Firm*—Shu Muk Lee; David L. Rose

(57) ABSTRACT

Compounds according to Formula (I) or a salt thereof are GABA-A Alpha 5 ligands useful for enhancing cognition:

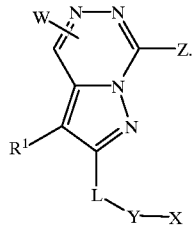

(I)

9 Claims, No Drawings

PYRAZOLO[1,5-D][1,2,4] TRIAZINES FOR ENHANCING COGNITION

This application claims the benefit of Great Britain Application No. 9927874.9, filed Nov. 25, 1999; Great Britain Application No. 0018651.0, filed Jul. 28, 2000; and Great Britain Application No. 0009602.4, filed Apr. 18, 2000.

BACKGROUND

The present invention relates to a class of substituted pyrazolotriazine derivatives and to their use in therapy. More particularly, this invention is concerned with substituted pyrazolo[1,5-d][1,2,4]triazine derivatives which are ligands for $GABA_A$ receptors containing the α5 subunit and are therefore useful in therapy where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one δ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101-108, that the benzodiazepine receptor inverse agonist β-CCM enhanced spatial learning in the Morris watermaze. However, β-CCM and other conventional benzodiazepine receptor inverse agonists are proconvulsant which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

SUMMARY OF THE INVENTION

The present invention is directed to compounds according to Formula (I) or a pharmaceutically acceptable salt thereof that are GABA-A Alpha 5 ligands useful for enhancing cognition:

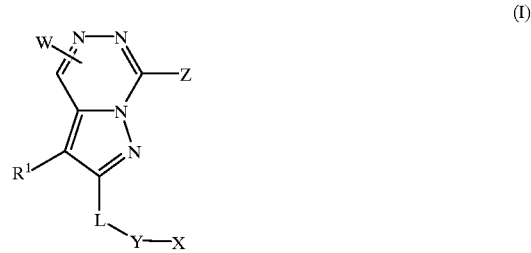

(I)

DETAILED DESCRIPTION OF THE INVENTION

It has now been discovered that use of an α5 receptor partial or full inverse agonist which is relatively free of activity at α1 and/or α2 and/or α3 receptor binding sites can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

The present invention provides a compound of formula I, or a salt thereof:

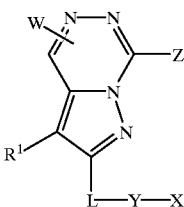
(I)

wherein $R^1$ represents halogen; or $C_{1-6}$alkyl, $C_{3-7}$cycloalkyl, $C_{4-7}$cycloalkenyl, $C_{6-8}$ bicycloalkyl, $C_{6-10}$aryl, $C_{3-7}$ heterocycloalkyl, heteroaryl defined as an aromatic ring containing either 6 atoms, 1, 2, or 3 of which are nitrogen, or 5 atoms, 1, 2 or 3 of which are independently chosen from oxygen, nitrogen or sulphur but not more than one of which is oxygen or sulphur, or di($C_{1-6}$)alkylamino, any of which groups may be optionally substituted with one or more substituents selected from halogen, $R^3$, $OR^3$, $OC(O)R^{3,}$ $NR^4R^5$, $NR^4R^5(C_{1-6})$alkyl, $NR^4R^5C(O)$, $NR^4R^5C(O)(C_{1-6})$alkyl, CN, cyano($C_{1-6}$)alkyl or $R^6$;

$R^3$ represents $C_{1-6}$alkyl, $C_{2-6}$alkenyl, $C_{2-6}$alkynyl, $C_{3-6}$cycloalkyl, $C_{3-6}$cycloalkyl($C_{1-6}$)alkyl, cyano($C_{1-6}$)alkyl, hydroxy$C_{1-6}$alkyl and $R^3$ is optionally mono, di or trifluorinated;

$R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with a nitrogen atom to which they are commonly attached, form a 4-7 membered heteroaliphatic ring containing the said nitrogen atom and optionally one other heteroatom selected from O, N and S, which ring is optionally substituted by one or more $R^3$ groups;

$R^6$ is $C_{6-10}$aryl, $C_{6-10}$aryl ($C_{1-6}$)alkyl, heteroaryl or heteroaryl($C_{1-6}$)alkyl, where heteroaryl is defined as above, and $R^6$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms;

L is O, S or $NR^n$ where $R^n$ is H, $C_{1-6}$alkyl or $C_{3-6}$cycloalkyl;

W is: $C_{1-6}$alkyl, $C_{2-6}$alkenyl or $C_{2-6}$alkynyl optionally substituted by one or more groups chosen from halogen, amino, nitro, cyano, hydroxy and halogen; hydrogen; halogen; amino; nitro; cyano; hydroxy; or halogen;

X is $NR^4R^5$; or X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene or pyridine ring and the heteroaromatic ring being optionally substituted by $R^x$ and/or $R^y$ and/or $R^z$, where $R^x$ is halogen, $R^3$, $OR^3$, $OC(O)R^3$, $C(O)OR^3$, $NR^4R^5$, $NR^4C(O)R^5$, OH, tri($C_{1-6}$alkyl)silyl$C_{1-6}$alkoxy$C_{1-4}$alkyl, CN or $R^6$, $R^y$ is halogen, $R^3$, $OR^3$, $OC(O)R^3$, $NR^4R^5$, $NR^4C(O)R^5$, $NR^4R^5(C_{1-6})$alkyl or CN and $R^z$ is $R^3$, $OR^3$ or $OC(O)R^3$, providing that when X is a pyridine derivative, the pyridine ring is optionally in the form of the N-oxide, and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

Y is optionally branched $C_{1-4}$alkylene optionally substituted by an oxo group or Y is a group $(CH_2)_jO$ wherein the oxygen atom is nearest the group X and j is 2, 3 or 4; and Z represents a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is also present, or a 6-membered heteroaromatic ring containing 2 or 3 nitrogen atoms with the exception of pyrazine, any of which rings may be optionally substituted with one or more substituents selected from halogen, $R^3$, $OR^3$, $OC(O)R^3$, $NR^4R^5$, $NR^4R^5(C_{1-6})$alkyl, $NR^4R^5C(O)$, $NR^4R^5C(O)(C_{1-6})$alkyl, CN, cyano($C_{1-6}$)alkyl or $R^6$.

The invention also provides a compound according to Formula I above, or a pharmaceutically acceptable salt thereof, wherein $R^1$, L, Y and Z are as defined above and X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by $R^x$ and/or $R^y$ and/or $R^z$, where $R^x$ is halogen, $R^3$, $OR^3$, $OC(O)R^3$, $NR^4R^5$, $NR^4C(O)R^5$, tri($C_{1-6}$alkyl)silyl$C_{1-6}$alkoxy$C_{1-4}$alkyl, CN or $R^6$, $R^y$ is halogen, $R^3$, $OR^3$, $OC(O)R^3$, $NR^4R^5$, $NR^4C(O)R^5$, $NR^4R^5(C_{1-6})$alkyl or CN and $R^z$ is $R^3$, $OR^3$ or $OC(O)R^3$, providing that when X is a pyridine derivative, the pyridine ring is optionally in the form of the N-oxide, and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

The expression "$C_{3-6}$cycloalkyl" as used herein includes cyclic propyl, butyl, pentyl and hexyl groups such as cyclopropyl and cyclohexyl.

The expression "$C_{3-6}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

The expression "$C_{1-4}$alkylene" as used herein refers to alkanediyl groups of up to 4 carbon atoms in which the unsatisfied valencies reside on the same carbon atom or on different carbon atoms.

Typical $C_{6-8}$ bicycloalkyl groups include bicyclo[2.1.1] hexyl and bicyclo[2.2.1]heptyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Unless otherwise specified, 5- and 6-membered heteroaromatic rings shall include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof A suitable 5-membered heteroaromatic ring containing four nitrogen atoms is tetrazolyl. Suitable 6-membered heteroaromatic rings containing three nitrogen atoms include 1,2,4-triazine and 1,3,5-triazine. When a heteroaromatic ring comprises a hydroxy group as a substituent, and keto-enol tautomerism is possible, both tautomers are included within the scope of the invention. Thus, for example, a 3-hydroxy-1,2,4-triazole ring will be considered equivalent to the 3-keto tautomer.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy, butoxy, pentoxy and hexoxy groups, including cyclopropylmethoxy. Derived expressions such as "$C_{2-6}$alkenyloxy", "$C_{2-6}$alkynyloxy", "$C_{1-4}$alkoxy", "$C_{2-4}$ alkenyloxy" and "$C_{2-4}$alkyloxy" should be construed in an analogous manner.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, the substituent $R^1$ in the compounds of formula I above represents halogen; or $C_{1-6}$ alkyl, aryl or heteroaryl, any of which groups may be optionally substituted. $R^1$ may be unsubstituted. $R^1$ may be mono substituted.

Suitable values for the substituent $R^1$ include bromo, tert-butyl, 1,1-dimethylpropyl, phenyl, pyridinyl, furyl or thienyl, any of which groups may be optionally substituted by one or two substituents.

Examples of typical optional substituents on the group $R^1$ include methyl, fluoro, chloro and trifluoromethyl. Particular substituents include fluoro, chloro and trifluoromethyl, especially fluoro.

Typical examples of suitable values for the group $R^1$ include bromo, tert-butyl, 1,1-dimethylpropyl, phenyl, pyridinyl, furyl and thienyl.

Further examples of suitable values for the substituent $R^1$ include methyl, ethyl, isopropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]hept-1-yl, pyrrolidinyl, methyl-pyrrolidinyl, piperidinyl, morpholinyl, thiomorpholinyl, pyridinyl, chloro-thienyl and diethylamino.

In preferred embodiments, the substituent $R^1$ represents bromo, thienyl, tert-butyl, phenyl or furyl, especially bromo, tert-butyl, phenyl or furyl. Favourably, $R^1$ represents tert-butyl. $R^1$ may also be hydroxytertbutyl or ethenyl.

$R^3$ is preferably $C_{1-4}$alkyl, $C_{2-4}$alkenyl, $C_{2-4}$alkynyl or hydroxy$C_{1-4}$alkyl and is optionally mono, di or trifluorinated. Most particularly $R^3$ is $C_{1-2}$alkyl, $C_2$alkenyl or hydroxy$C_{1-2}$alkyl optionally substituted with one, two or three halogen atoms.

$R^4$ and $R^5$ are preferably each independently hydrogen, $C_{1-4}$alkyl, $C_{2-4}$alkenyl or $C_{2-4}$alkynyl or $R^4$ and $R^5$, together with the nitrogen atom to which they are attached, form a 4-6 membered heteroaliphatic ring containing the said nitrogen atom and optionally one other heteroatom chosen from oxygen and nitrogen.

$R^6$ is preferably phenyl or pyridyl, optionally substituted by halogen, or $C_{1-4}$alkyl. $R^6$ is especially pyridyl.

Preferably L is an oxygen atom. L may also be S or NR'' in which R'' is preferably hydrogen or methyl. R'' may be hydrogen.

W is generally $C_{1-4}$alkyl optionally substituted by halogen or hydroxy; or W is hydrogen, halogen or hydroxy. W is particularly hydrogen or $C_{1-6}$alkyl, especially methyl or hydrogen. Generally W is hydrogen.

X may be a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene or pyridine ring and the heteroaromatic ring being optionally substituted by $R^x$ and/or $R^y$ and/or $R^z$, where $R^x$ is halogen, $R^3$, $OR^3$, $OC(O)R^3$, $NR^4R^5$, $NR^4C(O)R^5$, OH, tri($C_{1-6}$alkyl)silyl$C_{1-6}$alkoxy$C_{1-4}$alkyl, CN or $R^6$, $R^y$ is halogen, $R^3$, $OR^3$, $OC(O)R^3$, $NR^4R^5$, $NR^4C(O)R^5$, $NR^4R^5(C_{1-6})$alkyl or CN and $R^z$ is $R^3$, $OR^3$ or $OC(O)R^3$, providing that when X is a pyridine derivative, the pyridine ring is optionally in the form of the N-oxide, and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl.

X is generally: pyridyl, pyrazinyl, pyridazinyl or pyrimidinyl optionally substituted by a halogen atom or a group $R^3$, $OR^3$, $NR^4R^5$ or a five membered heteroaromatic ring containing 1, 2 or 3 nitrogen atoms, and X is optionally fused to a benzene ring; a 5-membered heteroaromatic ring containing 2 or 3 heteroatoms chosen from oxygen, sulphur and nitrogen, at most one of the heteroatoms being oxygen or sulphur, which is unsubstituted or substituted by one, two or three groups independently chosen from halogen and $R^3$, or which is substituted by a pyridyl, phenyl or benzyl ring which ring is optionally independently substituted by one, two or three halogen atoms or $C_{1-6}$alkyl or $CF_3$ groups; or phenyl optionally substituted by one, two or three independently chosen halogen atoms.

Alternatively, X may represent a 5-membered heteroaromatic ring containing 2 or 3 heteroatoms chosen from oxygen, sulphur and nitrogen, at most one of the heteroatoms being oxygen or sulphur, which is fused to a benzene or pyridine ring, or which is substituted by $NH_2$ or by OH which may exist as the keto tautomer; or X may represent a tetrazole ring bearing a $C_{1-4}$alkyl substituent.

When X is a substituted 6-membered heteroaromatic ring: $R^x$ is preferably halogen, $R^3$, $OR^3$, $NR^4R^5$ or a five-membered heteroaromatic ring containing 1, 2 or 3 nitrogen atoms and more preferably methyl, $CF_3$, methoxy, bromine, chlorine, isopropoxy, dimethylamino or a five-membered heterocyclic ring containing 1, 2 or 3 nitrogen atoms; and $R^y$ and $R^z$ are preferably absent.

When X is a substituted 5-membered heteroaromatic ring: $R^x$ is preferably halogen, $R^3$ or a pyridyl, phenyl or benzyl ring, which ring is optionally independently substituted by one, two or three halogen atoms or $C_{1-6}$alkyl or $CF_3$ groups, and more preferably $R^x$ is methyl, $CF_3$, chlorine or a phenyl, pyridyl or benzyl ring which ring is unsubstituted or substituted by chlorine or $CF_3$; and $R^Y$ and $R^z$ are preferably halogen or $R^3$ or are absent, and more preferably are methyl, $CF_3$ or chlorine, or are absent.

In one embodiment X is substituted by $CH_2NR^4R^5$ or $CH_2CH_2NR^4R^5$.

Specific values of X are 2-pyridyl, 1-methyl-1,2,4-triazol-3-yl, 2-methyl-1,2,4-triazol-3-yl, 1-methyl-1,2,3-triazol-4-yl, 5-methylisoxazol-3-yl, 1,2,4-oxadiazol-3-yl, and 2-methylthiazol-4-yl.

Further specific values of X are 1-methyl-1,2,3-triazol-5-yl, 5-oxo-1H, 4H-1,2,4-triazol-3-yl, 6-trifluoromethylpyrid-3-yl, 1-methylimidazol-2-yl, thiazol-4-yl, 2-aminothiazol-4-yl, 5-amino-1,2,4-thiadiazol-3-yl, pyridazin-3-yl, pyrazinyl, quinoxalin-2-yl, pyrimidin-4-yl, 1-methyltetrazol-5-yl, 5-(pyrid-4-yl)-2H-1,2,4-triazol-3-yl, oxazolo[4,5-b]pyridine-2-yl, 2-methylpyrazol-3-yl, 1-methylpyrazol-3-yl and pyrimidin-5-yl.

Yet further specific examples of X are 5-(piperidin-1-ylmethyl)pyridin-2-yl, 2-(2-(azetidin-1-yl)ethyl)pyridin-5-yl, 2-(2-(morpholin-4-yl)ethyl)pyridin-5-yl, 2-(2-(piperazin-1-yl)ethyl)pyridin-5-yl, 2-(2-(piperidin-1-yl)ethyl)pyridin-5-yl, 2-(2-(N,N-dimethylamino)ethyl)pyridin-5-yl, 2-(2-aminoethyl)pyridin-5-yl, 2-(2-aminoethyl)-1,2,4-triazol-3-yl, 2-(morpholin-4-ylmethyl)pyridin-5-yl, 2-hydroxymethylpyridin-5-yl, 5-(4-methylpiperazin-1-ylmethyl)pyridin-2-yl, 5-(azetidin-1-ylmethyl)pyridin-2-yl, 5-(morpholin-4-ylmethyl)pyridin-2-yl, 4-hydroxymethyl-1-methyl-1,2,3-triazol-5-yl, 5-aminomethylpyridin-2-yl, 5-(N,N-dimethylaminomethyl)pyridin-2-yl, 1-methyl-3-hydroxymethyl-1,2,4-triazol-5-yl, 1-methyl-3-(morpholin-4-ylmethyl)-1,2,4-triazol-5-yl, 1-methyl-3-(piperidin-1-ylmethyl)-1,2,4-triazol-5-yl, 6-hydroxymethylpyridin-2-yl, 6-(2-(morpholino-4-yl)ethyl)pyridin-2-yl, 6-(2-(piperazin-1-yl)ethyl)pyridin-2-yl, 5-trifluoromethylpyridin-2-yl, 6-(2-(piperidin-1-yl)ethyl)pyridin-2-yl, 1-methyl-3-(azetidin-1-ylmethyl)-1,2,4-triazol-5-yl, 1-methyl-3-((2,6-cisdimethylpiperidin-1-yl)methyl)-1,2,4-triazol-5-yl, 2-methyl-3-hydroxymethyl-1,2,4-triazol-5-yl, 2-methyl-3-(N,N-dimethylaminomethyl)-1,2,4-triazol-5-yl, 2-methyl-3-(N,N-diethylaminomethyl)-1,2,4-triazol-5-yl, 1-methyl-3-(N,N-dimethylaminomethyl)-1,2,4-triazol-5-yl, 1-methyl-3-(N,N-diethylaminomethyl)-1,2,4-triazol-5-yl, 1-methyl-3-(2-(N,N-diethylamino)ethyl)-1,2,4-triazol-5-yl, 5-(N-ethylaminomethyl)pyridin-2-yl, 5-(N,N-diethylaminomethyl)pyridin-2-yl and dimethylamino.

Apt values for Y include $CH_2$, $CH(CH_3)$, $CH_2CH_2$ and $CH_2CH_2CH_2$ optionally substituted by an oxo group, and $CH_2CH_2O$ and $CH_2CH_2CH_2O$. For example, Y can be $CH_2$, $CH_2CH_2$, $CH_2CH_2CH_2$, $CH_2CH_2O$ or $CH_2CH_2CH_2O$. Preferably Y is $CH_2$ or $CH_2CH_2$ and most preferably $CH_2$. Y may be $CH_2C(O)$.

From the foregoing it will be understood that particularly suitable groups L-Y-X are $OCH_2X$ groups where X is pyridyl or triazolyl, particularly 1,2,4-triazol-3-yl substituted with methyl in the 1- or 2-position.

Suitable values for Z include optionally substituted pyrimidinyl, triazinyl, pyrrolyl, oxazolyl, isoxazolyl, thiazolyl, isothiazolyl, oxadiazolyl and thiadiazolyl groups.

Z is very aptly an optionally substituted 5-membered heteroaromatic ring containing one oxygen and one or two nitrogen ring atoms.

Favoured values for Z include optionally substituted isoxazoles and oxadiazoles.

Typical substituents on Z include $C_{1-6}$alkyl, $C_{3-6}$cycloalkyl, hydroxy$C_{1-6}$alkyl, pyridyl, thienyl or amino, particularly methyl, ethyl, isopropyl, cyclopropyl, thienyl or pyridyl.

Z may be unsubstituted.

Z may very aptly be substituted by methyl.

Particular values of Z include 5-methylisoxazol-3-yl.

Further specific values of Z are 5-ethenylisoxazol-3-yl, 5-hydroxymethylisoxazol-3-yl, 5-(2-aminoethyl)isoxazol-3-yl, 5-aminomethylisoxazol-3-yl, 5-(2-(tertiarybutoxycarbonylamino)ethyl)isoxazol-3-yl, iodo, 5-(2-hydroxyethyl)isoxazol-3-yl, 5-(2-(azetidin-1-yl)ethyl)isoxazol-3-yl and 5-(2-(morpholin-4-yl)ethyl)isoxazol-3-yl.

A particular sub-class of compounds according to the invention is represented by the compounds of formula IIA, and pharmaceutically acceptable salts thereof:

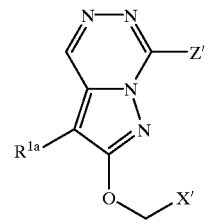

IIA wherein
$R^{1a}$ represents bromo, tert-butyl, 1,1-dimethylpropyl, phenyl, fluorophenyl, difluorophenyl, chlorophenyl, trifluoromethylphenyl, pyridinyl, furyl or thienyl;

X' represents phenyl, pyrazolyl, isoxazolyl, thiazolyl, imidazolyl, thiadiazolyl, benzimidazolyl, oxadiazolyl, triazolyl, tetrazolyl, pyridinyl, pyridazinyl, oxazolopyridinyl, pyrimidinyl, pyrazinyl, quinolinyl, isoquinolinyl or quinoxalinyl, any of which groups may be optionally substituted by one or more of $C_{1-6}$ alkyl, amino, pyridyl, $CF_3$, aryl($C_{1-6}$)alkyl, pyridyl($C_{1-6}$)alkyl, halogen, cyano, cyano($C_{1-6}$)alkyl, hydroxymethyl, $C_{1-6}$alkoxy, $C_{3-6}$cycloalkyl($C_{1-6}$)alkoxy, hydroxy or the keto tautomer thereof, di($C_{1-6}$)alkylamino($C_{1-6}$)alkyl, amino($C_{1-6}$)alkyl, N-($C_{1-6}$)alkylpiperidinyl, pyrrolidinyl($C_{1-6}$)alkyl, piperazinyl ($C_{1-6}$)alkyl and morpholinyl($C_{1-6}$)alkyl; and Z' represents a 5-membered heteroaromatic ring containing one oxygen and one or two nitrogen ring atoms which is optionally substituted with $C_{1-6}$alkyl or $C_{1-6}$alkoxy.

In a subset of the compound of Formula IIA, X' represents phenyl, pyrazolyl, isoxazolyl, thiazolyl, imidazolyl, benzimidazolyl, triazolyl, tetrazolyl, pyridinyl, pyridazinyl, oxazolopyridinyl, pyrimidinyl, pyrazinyl, quinolinyl, isoquinolinyl or quinoxalinyl, any of which groups may be optionally substituted by one or more of $C_{1-6}$ alkyl, $CF_3$, aryl($C_{1-6}$)alkyl, pyridyl($C_{1-6}$)alkyl, halogen, cyano, cyano($C_{1-6}$)alkyl, hydroxymethyl, $C_{1-6}$alkoxy, $C_{3-6}$cycloalkyl($C_{1-6}$)alkoxy, hydroxy or the keto tautomer thereof, di($C_{1-6}$)alkylamino($C_{1-6}$)alkyl, amino($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl.

Illustrative values of specific substituents on the group X' include methyl, ethyl, n-propyl, isopropyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, N-methylpiperidinyl, pyrrolidinylethyl, piperazinylethyl and morpholinylmethyl.

Further illustrative values of specific substituents on the group X' include trifluoromethyl, amino, pyridyl and hydroxy or its keto tautomer.

Selected substituents for the group X' include methyl, ethyl, n-propyl, and isopropyl, especially methyl.

Further selected substituents for the group X' include trifluoromethyl, amino, pyridyl and hydroxy or its keto tautomer.

Specific values of X' include pyridyl, methyl-triazolyl, ethyl-triazolyl, propyl-triazolyl and isopropyl-triazolyl.

Further specific values of X' include 1,2,4-oxadiazolyl, methyl-thiazolyl, 5-hydroxy-1,2,4-triazolyl (which is equivalent to 5-oxo-1H, 4H-1,2,4-triazolyl), trifluoromethylpyridyl, methyl-imidazolyl, thiazolyl, amino-thiazolyl, amino-1,2,4-thiadiazolyl, pyridazinyl, pyrazinyl, quinoxalinyl, pyrimidinyl, methyl-tetrazolyl, pyridyl-triazolyl, oxazolopyridinyl and methyl-pyrazolyl.

A favoured value of X' is methyl-triazolyl.

A particular subset of the compounds of formula IIA above is represented by the compounds of formula IIB, and pharmaceutically acceptable salts thereof:

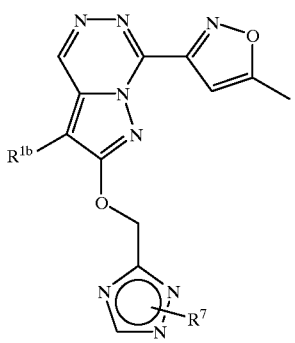

IIB wherein
$R^{1b}$ represents bromo, thienyl, tert-butyl, phenyl or furyl; and
$R^7$ represents hydrogen, methyl, ethyl, n-propyl or isopropyl.

In a subset of the compound of Formula IIB, $R^{1b}$ represents bromo, tert-butyl, phenyl or furyl.

In a particular embodiment of the compounds of formula IIB above, $R^7$ represents methyl.

Particular compounds within the scope of the present invention include:

7-(5-methylisoxazol-3-yl)-2-(1-methyl-1H-[1,2,4]triazol-3-ylmethoxy)-3-phenylpyrazolo[1,5-d][1,2,4]triazine;

3-tert-butyl-7-(5-methylisoxazol-3-yl)-2-(1-methyl-1H-[1,2,4]triazol-3-ylmethoxy)pyrazolo [1,5-d][1,2,4]triazine;

3-tert-butyl-7-(5-methylisoxazol-3-yl)-2-(1-methyl-1H-[1,2,4]triazol-5-ylmethoxy)pyrazolo[1,5-d][1,2,4]triazine;

3-tert-butyl-7-(5-methylisoxazol-3-yl)-2-(pyrid-2-ylmethoxy)pyrazolo[1,5-d][1,2,4]triazine;

3-tert-butyl-7-(5-methylisoxazol-3-yl)-2-(pyrid-3-ylmethoxy)pyrazolo[1,5-d][1,2,4]triazine; and 3-tert-butyl-7-(5-methylisoxazol-3-yl)-2-(pyrid-4-ylmethoxy)pyrazolo[1,5-d][1,2,4]triazine;

and the pharmaceutically acceptable salts thereof.

The compounds of the present invention have a good binding affinity (Ki) for the α5 subunit of the $GABA_A$ receptor. In a preferred embodiment the compounds of the invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment of the human body. Preferably the treatment is for a condition associated with $GABA_A$ receptors comprising the α5 subunit and/or for the enhancement of cognition. Preferably the condition is a neurological deficit with an associated cognitive disorder such as a dementing illness such as Alzheimer's disease. Other conditions to be treated include cognition deficits due to traumatic injury, stroke, Parkinson's disease, Downs syndrome, age related memory deficits, attention deficit disorder and the like.

The present invention further provides the use of a compound of the present invention in the manufacture of a medicament for the enhancement of cognition, preferably in a human suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For the enhancement of cognition, a suitable dosage level is about 0.01 to 250 mg/kg per day, preferably about 0.01 to 100 mg/kg of body weight per day, especially about 0.01 to 5 mg/kg of body weight per day, more particularly from 0.02 to 2.5 mg/kg of body weight per day. The compounds may be administered on a regimen of 1 to 4 times per day. In some cases, however, dosage outside these limits may be used. A typical body weight is 70 kg.

The compounds in accordance with the invention may be prepared by a process which comprises cyclising a compound of formula III:

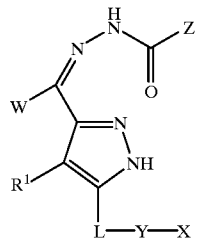

(III)

wherein $R^1$, L, W, X, Y and Z are as defined above.

The cyclisation of compound III may conveniently be effected by heating compound III to an elevated temperature, e.g. (i) a temperature in the region of 180–200° C., in the presence of a high-boiling medium such as Dowtherm A; or (ii) at the reflux temperature of an inert solvent such as xylene, optionally in the presence of a proton source such as triethylamine hydrochloride.

The intermediates of formula III above may be prepared by reacting a compound of formula IV with a hydrazide derivative of formula V:

(IV)

(V)

wherein $R^1$, W, L, X, Y and Z are as defined above.

The reaction between compounds IV and V is conveniently effected by heating the reactants, optionally in the presence of a proton source such as triethylamine hydrochloride, typically at reflux in an inert solvent such as xylene.

In another procedure, the compounds of formula I as defined above wherein L represents O may be prepared by a process which comprises reacting a compound of formula VI with a compound of formula VII:

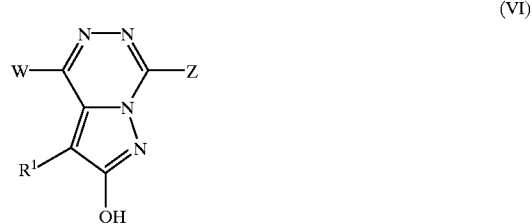

(VI)

(VII)

wherein $R^1$, W, X, Y and Z are as defined above, and G represents a suitable leaving group.

The leaving group G is suitably a halogen atom, typically chlorine.

The reaction between compounds VI and VII is conveniently effected by stirring the reactants in a suitable solvent, typically N,N-dimethylformamide, in the presence of a base such as cesium carbonate or potassium carbonate.

Similarly, the intermediates of formula IV wherein L represents O may be prepared by reacting a compound of formula VII as defined above with a compound of formula VIII or its keto tautomer:

(VIII)

wherein $R^1$ is as defined above; under conditions analogous to those described above for the reaction between compounds VI and VII; followed by oxidation.

Oxidation of the $CH_2OW$ side-chain in the intermediate resulting from the reaction between compounds VII and VIII to the aldehyde CHO side-chain in the corresponding intermediate of formula IV is suitably effected by treatment with manganese dioxide, in which case the reaction is conveniently carried out in chloroform at an elevated temperature in the region of 70° C.

An alternative methodology can be used to make compounds where X is substituted by $NR^4R^5C_{1-6}$alkyl. For example when the $C_{1-6}$alkyl group is $CH_2$ a compound of formula XVI:

HO—Y—X—$CH_2$—OP         XVI where X and Y are as defined above and P is a suitable protecting group such as TBS, is chlorinated, for example with thionylchloride generally in dichloromethane at about 0° C. for about half an hour to give a compound of formula XVII:

Cl—Y—X—$CH_2$OP         XVII where X, Y and P are as defined above. This compound is coupled to a compound of formula VI as described above to give a compound of formula XVIII:

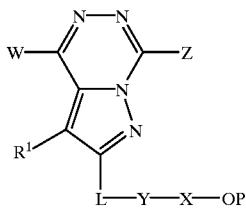

XVIII wherein L, $R^1$, W, X, Y, Z and P are as defined above. The compound of formula XVIII can be deprotected to give a compound of formula I in which X is substituted by $CH_2OH$. This compound can be mesylated, for example with MsCl generally in a solvent such as dichloromethane in the presence of a base such as triethylamine for about one hour at about room temperature. The resulting compound can be reacted with $HNR^4R^5$, where $R^4$ and $R^5$ are as defined above, to give the desired compound of formula I in which X is substituted by —$CH_2NR^4R^5$.

When the $C_{1-6}$alkyl is $CH_2CH_2$ a compound of formula XIX:

Cl—Y—X—$CHCH_2$         XIX wherein X and Y are as defined above, is coupled to a compound of formula VI as described above to give a compound of formula XX:

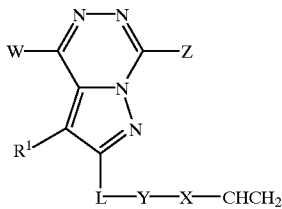

XX wherein L, $R^1$, W, X, Y and Z are as defined above. Reacting with $HNR^4R^5$, where $R^4$ and $R^5$ are as described above, generally in a sealed tube in the presence of an acid such as acetic acid, and a solvent, such as methanol, produces the desired compound of formula I in which X is substituted by —$CH_2CH_2NR^4R^5$.

Compounds where the $C_{1-6}$alkyl group in $NR^4R^5C_{1-6}$alkyl is other than $CH_2$ and $CH_2CH_2$ can be made by analogous methods.

In a further procedure, the compounds of formula I as defined above may be prepared by a process which comprises reacting a compound of formula IX with a compound of formula X:

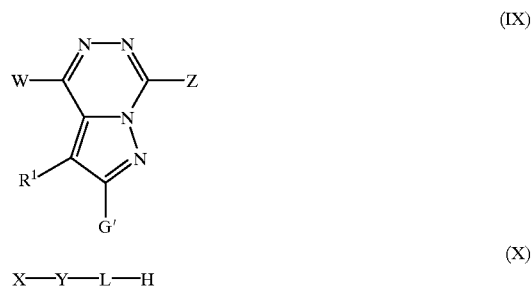

(IX)

X—Y—L—H         (X)

wherein $R^1$, L, W, X, Y and Z are as defined above, and G' represents a suitable leaving group.

The leaving group G' is typically an arylsulfonyloxy moiety, e.g. p-toluenesulfonyloxy (tosyloxy).

The reaction between compounds IX and X is conveniently effected by stirring the reactants in a suitable solvent, typically N,N-dimethylformamide, in the presence of a base such as sodium hydride.

The intermediates of formula IX above may be prepared by reacting a compound of formula V as defined above with a compound of formula XI:

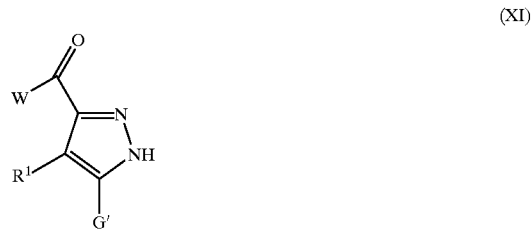

(XI)

wherein W, Z and G' are as defined above.

The reaction between compounds V and XI is conveniently effected by heating the reactants, optionally in the presence of a proton source such as triethylamine hydrochloride, typically at reflux in an inert solvent such as xylene.

In a still further procedure, the compounds of formula I as defined above may be prepared by a process which comprises reacting a compound of formula XII with a compound of formula XIII:

$R^1$—M         (XII)

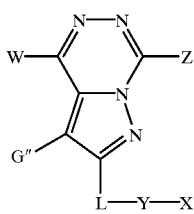

(XIII)

wherein R¹, L, W, X, Y and Z are as defined above, G" represents a suitable leaving group, and M represents —B(OH)$_2$ or a cyclic ester thereof formed with an organic diol, e.g. 1,3-propanediol, or M represents —Sn(Alk)$_3$ in which Alk represents a C$_{1-6}$ alkyl group, typically n-butyl; in the presence of a transition metal catalyst.

The leaving group G" is typically a halogen atom, e.g. bromo.

Where M represents —B(OH)$_2$ or a cyclic ester thereof, the transition metal catalyst is suitably tris(dibenzylideneacetone)palladium(O), in which case the reaction between compounds XII and XIII is conveniently effected at an elevated temperature in a solvent such as 1,4-dioxane, typically in the presence of tri-tert-butylphosphine and cesium carbonate.

Where M represents —Sn(Alk)$_3$, the transition metal catalyst is suitably tetrakis(triphenylphosphine)palladium (O), in which case the reaction between compounds XII and XIII is conveniently effected at an elevated temperature in a solvent such as 1,4-dioxane, typically in the presence of copper(I) iodide.

The compounds of formula XIII above wherein L represents O may be prepared by reacting a compound of formula VII as defined above with a compound of formula XIV:

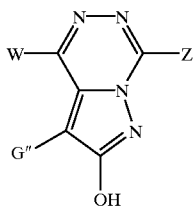

(XIV)

wherein W, Z and G" are as defined above; under conditions analogous to those described above for the reaction between compounds VI and VII.

The intermediates of formula XIV in which the leaving group G" represents bromo may be prepared by bromination of a compound of formula XV:

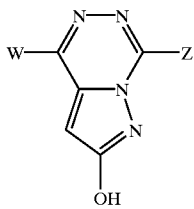

(XV)

wherein W and Z are as defined above.

The bromination reaction is conveniently effected by treating the appropriate compound of formula XV with bromine, typically in glacial acetic acid.

The intermediates of formula VII and X above may be prepared by the procedures described in WO 98/04559, or by methods analogous thereto.

Where they are not commercially available, the starting materials of formula V, VI, VIII, XI, XII, XV, XVI, XIX and HNR⁴R⁵ may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. Indeed, as will be appreciated, the compounds of formula XIII in which G" is halogen are compounds according to the invention in their own right. By way of example, a compound of formula I initially obtained wherein X is unsubstituted may be converted into a corresponding compound wherein X is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein the X substituent is substituted by a halogen atom, e.g. chloro, may be converted into the corresponding compound wherein the X substituent is substituted by a di(C$_{1-6}$)alkylamino moiety by treatment with the appropriate di(C$_{1-6}$)alkylamine, typically with heating in a solvent such as 1,4-dioxane in a sealed tube.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The compounds in accordance with this invention potently inhibit the binding of [3H]-flumazenil to the benzodiazepine binding site of human GABA$_A$ receptors containing the α5 subunit stably expressed in Ltk-cells.

Reagents

Phosphate buffered saline (PBS).

Assay buffer: 10 mM KH$_2$PO$_4$, 100 mM KCl, pH 7.4 at room temperature.

[3H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [3H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant Ki can be calculated for each test compound.

The compounds of the accompanying Examples were tested in the above assay, and all were found to possess a Ki value for displacement of [3H]Ro 15-1788 from the α5 subunit of the human $GABA_A$ receptor of 100 nM or less, most were at 50 nM or less, many were at 10 nM or less and some were at 1 nM or less.

The compounds of the present invention can be shown to enhance cognition in the rat water maze test (Morris, Learning and Motivation, 1981, 12, 239ff). This has been demonstrated for at least one compound described herein. Further details of methodology for demonstrating that the present compounds enhance cognition can be found in WO-A-9625948.

The following Examples, the structures of all of which were confirmed by nmr, illustrate the present invention:

EXAMPLE 1

7-(5-Methylisoxazol-3-yl)-2-(1-methyl-1H-[1,2,4]triazol-3-ylmethoxy)-3-phenylpyrazolo [1,5-d][1,2,4]triazine Step 1: 5-Hydroxymethyl-4-phenylpyrazol-3-one 4-Hydroxy-3-phenyl-2-furanone (5 g, 28.3 mmol) was dissolved in EtOH (60 mL) with hydrazine hydrate (6.9 mL, 0.142 mol) and heated at 140° C. in a sealed tube for 64h. Further hydrazine hydrate (4 mL, 82 mmol) was added and the mixture heated at 140° C. for another 48h. The solvent was evaporated and the residue was chromatographed on silica, eluting with 10% MeOH/DCM, followed by 20% MeOH/DCM to afford the title compound (3.62 g, 67%) as a cream solid. mp 165–168° C. $^1$H NMR (400 MHz, $d_6$-DMSO) δ4.45 (2H, d, J=5.0 Hz), 5.30 (1H, t, J=5.0 Hz), 7.15 (1H, t, J=7.4 Hz), 7.33 (2H, t, J=7.6 Hz), 7.55 (2H, d, J=7.7 Hz), 9.90 (1H, brs), 11.75 (1H, brs).

Step 2: 5-Hydroxymethyl-3-(1-methyl-1H-[1,2,4]triazol-3-ylmethoxy)-4-phenylpyrazole To a solution of the pyrazolone (1.2 g, 6.3 mmol) in DMF (20 mL) was added finely ground $K_2CO_3$ (5.23 g, 39 mmol) and 3-chloromethyl-1-methyl-1H[1,2,4]triazole hydrochloride (1.06 g, 6.3 mmol) and the reaction mixture was heated at 50° C. for 6h. After cooling the mixture was filtered and the filtrate evaporated. The residue was chromatographed on silica eluting with 10% MeOH/DCM to afford the title compound (0.60 g, 33%) as a colourless foam. $^1$H NMR (400 MHz, $d_6$-DMSO) δ4.00 (3H, s), 4.63 (2H, d, J=5.2 Hz), 5.35 (2H, s), 5.55 (1H, t, J=5.2 Hz), 7.32 (1H, t, J=7.3 Hz), 7.43–7.51 (2H, m), 7.65 (2H, d, J=7.3 Hz), 8.58 (1H, s), 12.23 (1H, s). MS (ES$^+$) 286 (M+1).

Step 3: 5-Formyl-3-(1-methyl-1H-[1,2,4]triazol-3-ylmethoxy)-4-phenylpyrazole

A mixture of the alcohol (0.6 g, 2.1 mmol) and manganese dioxide (0.73 g, 8.4 mmol) in $CHCl_3$ (30 mL) was heated at reflux for 24h. Further manganese dioxide (0.37 g, 4.2 mmol) was added and the mixture heated at reflux for 24h. After cooling the mixture was filtered through "Hyflo" and the filtrate evaporated. The residue was chromatographed on silica eluting with 10% MeOH/DCM to give the title compound (0.47 g, 78%) as a yellow solid. mp 202–205° C. $^1$H NMR (400MHz, $d_6$-DMSO) δ 3.84–3.87 (3H, m), 5.26–5.33 (2H, m), 6.47 and 6.72 (1H, 2×d, J=7.4 and 8.6 Hz), 7.26–7.42 (3H, m), 7.65 and 7.86 (1H, 2×d, J=7.4 and 8.6 Hz), 7.69–7.71 (2H, m), 8.46–8.98 (1H, m).

Step 4: 5-(5-Methylisoxazol-3-yl)-2-(1-methyl-1H-[1,2,4]triazol-3-ylmethoxy)-3-phenylpyrazolo[1,5-d][1,2,4]triazine To a suspension of the aldehyde (0.15 g, 0.53 mmol) in xylene (5 mL) was added 5-methylisoxazol-3-yl hydrazide (75 mg, 0.53 mmol) and triethylamine hydrochloride (73 mg, 0.53 mmol). This mixture was heated at reflux for 1h. The solvent was evaporated and the residue partitioned between DCM (2×50 mL) and water (50 mL). The combined organic phases were dried ($Na_2SO_4$) and evaporated. The residue was chromatographed on silica eluting with 5% MeOH/DCM to afford the title compound (34 mg, 17%) as a yellow solid. mp 194–196° C. Found: C, 55.44; H, 4.13; N, 26.93%. $C_{19}H_{16}N_8O_2$. 1.2($H_2O$) requires: C, 55.66; H, 4.52; N, 27.33%. $^1$H NMR ($CDCl_3$, 360 MHz) δ2.62 (3H, s), 3.94 (3H, s), 5.68 (2H, s), 7.13 (1H, s), 7.35–7.39 (1H, m), 7.46–7.50 (2H, m), 7.70–7.73 (2H, m), 8.04 (1H, s), 9.42 (1H, s). MS (ES$^+$) 389 (M+1).

EXAMPLE 2

3-tert-Butyl-7-(5-methylisoxazol-3-yl)-2-(1-methyl-1H-[1,2,4]triazol-3-ylmethoxy)pyrazolo[1,5-d][1,2,4]triazine Step 1: 4-tert-Butyl-5-hydroxymethyl-pyrazol-3-one 3-tert-Butyl-4-hydroxy-2-furanone (6.6 g, 42 mmol) was dissolved in EtOH (75 mL) with hydrazine hydrate (6.6 mL, 0.21 mol) and was heated at reflux for 16h. The solvent was evaporated and the residue azeotroped with xylene (3×50 mL) to afford the title compound (7.2 g, 100%) as a colourless solid. mp 169–172° C. $^1$H NMR (360 MHz, $d_6$-DMSO) δ1.26 (9H, s), 4.41 (2H, d, J=5.2 Hz), 4.97–5.01 (1H, m), 9.30 (1H, br s), 11.05 (1H, br s). MS (ES$^+$) 171 (M+1).

Step 2: 4-tert-Butyl-5-hydroxymethyl-3-[(4-methylphenyl) sulphonyloxy]pyrazole

To a suspension of the pyrazolone (7.2 g, 42 mmol) in DCM (140 mL) was added 4-toluene sulphonyl chloride (9.7 g, 51 mmol) followed by Et$_3$N (7.7 mL, 55 mmol) dropwise. The mixture was stirred at room temperature for 16h. The mixture was washed with brine (150 mL) and dried (Na$_2$SO$_4$) and evaporated. The residue was chromatographed on silica with 5 to 10% MeOH/DCM to afford the title compound (9.3 g, 68%) as a cream solid. mp. 62–65° C. $^1$H NMR (400MHz, d$_6$-DMSO) δ1.28 (9H, s), 2.43 (3H, s), 4.49 (2H, d, J=5.2 Hz), 5.32 (1H, t, J=5.2 Hz), 7.48 (2,d, J=8.2 Hz), 7.86 (2H, d, J=8.2 Hz), 12.28 (1H, s). MS (ES$^+$) 325 (M+1).

Step 3: 4-tert-Butyl-5-formyl-3-[(4-methylphenyl) sulphonyloxy]pyrazole

In the same way as described in Example 1, Step 3 the title compound (9.2 g, 100%) was obtained a pale yellow foam. $^1$H NMR (CDCl$_3$, 400 MHz) δ1.37 and 1.49 (9H, 2xs), 2.47 (3H, s), 3.80–3.90 (0.7H, br m), 6.70 (0.7H, s), 7.37 (2H, d, J=8.0 Hz), 7.92–7.97 (2H, m), 10.10–10.25 (0.6H, m). MS (ES$^+$) 323 (M+1).

Step 4: 3-tert-Butyl-7-(5-methylisoxazol-3-yl)-2-[(4-methylphenyl)sulphonyloxy]pyrazolo[1,5-d][1,2,4]triazine To a suspension of the aldehyde (1.5 g, 4.7 mmol) in xylene (100 mL) was added 5-methylisoxazol-3-yl hydrazide and this mixture was heated at reflux for 24h. After cooling the solvent was evaporated and the residue triturated with ether. The resultant solid was collected by filtration to afford the title compound (1.3 g, 67%) as a brown solid. mp. 212–216° C. $^1$H NMR (400MHz, CDCl$_3$) δ1.57 (9H, s), 2.51 (3H, s), 2.61 (3H, s), 6.81 (1H, s), 7.44 (2H, d, J=8.0 Hz), 8.18 (2H, d, J=8.0 Hz), 9.50 (1H, s). MS (ES$^+$) 428 (M+1).

Step 5: 3-tert-Butyl-2-hydroxy-7-(5-methylisoxazol-3-yl)-pyrazolo[1,5-d][1,2,4]triazine To a suspension of the tosylate (11.85 g, 28 mmol) in MeOH (200 mL) was added NaOH solution (4N, 13.9 mL, 56 mmol). This mixtue was stirred at room temperature for 16h. The solvent was evaporated and the residue dissolved in water (200 mL). The mixture was acidified (1M HCl) and the resultant solid collected by filtration. The solid was triturated with MeOH and collected by filtration to afford the title compound (5.20 g, 69%) as a pale yellow solid. mp. 275–278° C. $^1$H NMR (360MHz, d$_6$-DMSO) δ1.46 (9H, s), 2.56 (3H, s), 6.95 (1H, s), 9.48 (1H, s), 12.03 (1H, s). MS (ES$^+$) 274 (M+1).

Step 6: 3-tert-Butyl-7-(5-methylisoxazol-3-yl)-2-(1-methyl-1H-[1,2,4]triazol-3-ylmethoxy)pyrazolo[1,5-d][1,2,4]triazine To a solution of the hydroxy pyrazolotriazine (0.1 g, 0.37 mmol) in DMF (5 mL) was added 3-chloromethyl-1-methyl-1H-[1,2,4]triazole hydrochloride (68 mg, 0.40 mmol) and finely ground K$_2$CO$_3$ (0.2 g, 1.47 mmol). This mixture was stirred at room temperature for 18h and then heated at 60° C. for 8h. The solvent was evaporated and the residue partitioned between DCM (2x50 mL) and water (50 mL). The combined organics were dried (Na$_2$SO$_4$) and evaporated. The residue was chromatographed on silica eluting with 5% MeOH/DCM to afford the title compound (76 mg, 56%), after trituration with ether, as a colourless solid. mp. 161–164° C. Found: C, 54.55; H, 5.37; N, 29.35%. C$_{17}$H$_{20}$N$_8$O$_2$. 0.475(H$_2$O) requires: C, 54.17; H, 5.60; N, 29.73%. $^1$H NMR (400MHz, CDCl$_3$) δ1.50 (9H, s), 2.59 (3H, s), 3.94 (3H, s), 5.57 (2H, s), 7.06 (1H, s), 8.04 (1H, s), 9.40 (1H, s). MS (ES$^+$) 369 (M+1).

EXAMPLE 3

3-tert-Butyl-7-(5-methylisoxazol-3-yl)-2-(1-methyl-1H-[1,2,4]triazol-5-ylmethoxy)pyrazolo[1,5-d][1,2,4]triazine In the same way as Example 2, Step 6, using 5-chloromethyl-1-methyl-1H-[1,2,4]triazole hydrochloride (37 mg, 0.22 mmol) the title compound (54 mg, 73%) was afforded as a cream solid. mp 171–174° C. Found: C, 55.70; H, 5.33; N, 30.60%. C$_{17}$H$_{20}$N$_8$O$_2$ requires: C, 55.43; H, 5.47; N, 30.42%. $^1$H NMR (400MHz, CDCl$_3$) δ1.50 (9H, s), 2.60 (3H, s), 4.05 (3H, s), 5.67 (2H, s), 6.92 (1H, s), 7.90 (1H, s), 9.42 (1H, s). MS (ES$^+$) 369 (M+1).

EXAMPLE 4

3-tert-Butyl-7-(5-methylisoxazol-3-yl)-2-(pyrid-2-ylmethoxy)pyrazolo[1,5-d][1,2,4]triazine In the same way as Example 2, Step 6, using 2-picolyl chloride hydrochloride (36 mg, 0.22 mmol), the title compound (47 mg, 64%) was afforded as a pale yellow solid. mp 175–178° C. Found: C, 61.40; H, 5.16; N, 22.30%. C$_{19}$H$_{20}$N$_6$O$_2$.0.1(CH$_2$Cl$_2$) requires: C, 61.52; H, 5.46; N, 22.54% $^1$H NMR (360MHz, CDCl$_3$) δ1.57 (9H, s), 2.59 (3H, s), 5.65 (2H, s), 6.91 (1H, s), 7.25–7.29 (1H, m), 7.55–7.60 (1H, m), 7.73–7.78 (1H, m), 8.62–8.64 (1H, m), 9.42 (1H, s). MS (ES$^+$) 365 (M+1).

EXAMPLE 5

3-tert-Butyl-7-(5-methylisoxazol-3-yl)-2-(pyrid-3-ylmethoxy)pyrazolo[1,5-d][1,2,4]triazine In the same way as Example 2, Step 6, using 3-picolyl chloride hydrochloride (33 mg, 0.20 mmol), the title compound (30 mg, 45%) was afforded as a pale yellow solid. mp 139–141° C. Found: C, 61.78; H, 5.30; N, 22.34%. C$_{19}$H$_{20}$N$_6$O$_2$.0.3(H$_2$O) requires: C, 61.71; H, 5.61; N, 22.72%. $^1$H NMR (400MHz, CDCl$_3$) δ1.51 (9H, s), 2.61 (3H, s), 5.55 (2H, s), 6.87 (1H, s), 7.32–7.36 (1H, m), 7.87–7.92 (1H, m), 8.58–8.62 (1H, m), 8.80–8.84 (1H, m), 9.40 (1H, m). MS (ES$^+$) 365 (M+1).

EXAMPLE 6

3-tert-Butyl-7-(5-methylisoxazol-3-yl)-2-(pyrid-4-ylmethoxy)pyrazolo[1,5-d][1,2,4]triazine In the same way as Example 2, Step 6, using 4-picolyl chloride hydrochloride (33 mg, 0.20 mmol) the title compound (32 mg, 48%) was obtained as a cream solid. mp. 119–121° C. Found: C, 62.37; H, 5.43; N, 22.86%. C$_{19}$H$_{20}$N$_6$O$_2$ requires C, 62.62; H, 5.53; N, 23.06%. $^1$H NMR (400MHz, CDCl$_3$), δ1.56 (9H, s), 2.59 (3H, s), 5.55 (2H, s), 6.82 (1H, s), 7.43 (2H, d, J=5.8 Hz), 8.65 (2H, d, J=5.8 Hz), 9.42 (1H, s). MS (ES$^+$) 365 (M+1).

EXAMPLE 7

3-Bromo-7-(5-methylisoxazol-3-yl)-2-(1-methyl-1H-[1,2,4]triazol-5-ylmethoxy)pyrazolo[1,5-d][1,2,4]triazine Step 1: Toluene-4-sulfonic acid 5-hydroxymethyl-1H-pyrazol-3-yl ester To a stirred suspension of 5-hydroxymethyl-1H-pyrazol-3-ol (*J. Heterocycl. Chem.*, 1979, 16, 505–508) (1.0245 g, 8.98 mmol) in anhydrous dichloromethane (50 ml), under nitrogen, was added p-toluenesulfonyl chloride (1.8825 g, 9.87 mmol), then dropwise over 5 min, anhydrous triethylamine (1.50 ml, 10.8 mmol). The mixture was stirred at room temperature for 16.5 h under nitrogen, then washed with brine (50 ml). The aqueous layer was further extracted with dichloromethane, and the combined organic extracts were dried (Na$_2$SO$_4$) and evaporated in vacuo. The residue was purified by flash chromatography (silica gel, 5–7%

MeOH/CH$_2$Cl$_2$) to afford 1.3067 g (54%) of the title compound as a pale green solid; $^1$H NMR (360 MHz, d$_6$-DMSO) δ2.42 (3H, s), 4.38 (2H, d, J=5.7 Hz), 5.32 (1H, t, J=5.7 Hz), 5.82 (1H, d, J=2.2 Hz), 7.47 (2H, d, J=8.3 Hz, 7.77 (2H, d, J=8.3 Hz), 12.55 (1H, s).

Step 2: Toluene-4-sulfonic acid 5-formyl-1H-pyrazol-3-yl ester

To a solution of toluene-4-sulfonic acid 5-hydroxymethyl-1H-pyrazol-3-yl ester (8 g, 30 mmol) in chloroform (800 mL) was added manganese dioxide (13 g, 150 mmol) and the suspension was heated at reflux for 20 h.

The cooled mixture was filtered through "Hyflo" washing with 1:1 CHCl$_3$:MeOH (hot) until all product eluted and the filtrate evaporated. The residue was triturated with hot MeOH (30 ml) cooled in the fridge and solid isolated by filtration and washed once with MeOH to give title compound (4.3 g, 54%) as a grey solid.

A second crop (0.5 g) of pink/grey solid was isolated from MeOH trituration of evaporated liquors. Total yield (4.8 g, 60%) MS (ES$^+$) 267 (M+1), TLC, silica, 3% MeOH/DCM rf=0.32.

Step 3: Toluene-4-sulfonic acid 7-(5-methylisoxazol-3-yl)pyrazolo[1,5-d][1,2,4]triazin-2-yl ester A stirred suspension of foregoing aldehyde (4 g, 15 mmol) and 3-methylisoxazol-5-yl hydrazide (2.2 g, 15 mmol) in xylene (150 mL) was heated at reflux for 4 h. The mixtures was evaporated to dryness and the residue suspended in Dowtherm A (100 mL) and heated at 200° C. for 4h. To the cooled mixture was added DCM (150 mL) and mixture poured onto large silica plug column and eluted with DCM:MeOH (100:0→98:2). Product isolated crude as a brown oil (3 g). Oil was purified by silica plug chromatography eluting with 0.5% MeOH:DCM to give title compound (2 g, 37%) as a brown solid. $^1$H NMR (400 MHz, d$_6$-DMSO) δ2.45 (3H, s), 2.58 (3H, s), 6.82 (1H, s), 7.00 (1H, s), 7.53 (2H, d, J=9.0 Hz), 7.94 (2H,d, J=8.4 Hz), 9.66 (1H, s) MS (ES$^+$372 (M+1).

Step 4: 7-(5-Methylisoxazol-3-yl)pyrazolo[1,5d][1,2,4]triazin-2-ol

To a stirred solution of the tosylate (2 g, 5,4 mmol) in MeOH (75 mL) was added NaOH solution (4N, 2.7 mL, 10.8 mmol) and the mixture stirred at rt for 1.5 h. The solvent was evaporated and the residue dissolved in water (50 mL). The mixture was acidified (1N HCl) and the resultant solid collected by filtration washing once with water. The solid was dried under vacuum to give title compound (1 g, 85%) as a brown solid. $^1$H NMR (400 MHz, d$_6$-DMSO) δ2.57 (3H, s), 6.39 (1H, s), 7.02 (1H, s), 9.42 (1H, s), 11.91 (1H, s). TLC silica 5% MeOH/DCM rf=0.32.

Step 5: 3-Bromo-7-(5-methylisoxazol-3-yl)pyrazolo[1,5-d][1,2,4]triazin-2-ol

To a stirred solution of foregoing pyrazole (1 g, 4.6 mmol) in AcOH (20 ml) was added bromine (0.26 mL, 5.10 mmol) dropwise. The mixture was stirred at rt for 1 h. Water (50 mL) was added and solid isolated by filtration, washed with water then diethyl ether and dried under vacuum to give title compound (1 g, 74%) as a brown solid. $^1$H NMR (360 MHz, d$_6$-DMSO) δ2.58 (3H s), 7.00 (1H, s), 9.41 (1H, s), 12.86 (1H, s). MS (ES$^+$) 296 (M+1).

Step 6: 3-Bromo-7-(5-methylisoxazol-3-yl)-2-(1-methyl-1H-[1,2,4]triazol-5-ylmethoxy)pyrazolo[1,5-d][1,2,4triazine To a stirred solution of foregoing hydroxy pyrazolotriazine (170 mg, 0.57 mmol) in anhydrous DMF (10 mL) was added 5-chloromethyl-1-methyl-1H-[1,2,4]triazole hydrochloride (106 mg, 0.63 mmol) and potassium carbonate (320 mg, 2.3 mmol). This mixture was stirred at rt under nitrogen for 24 h, and then heated at 60° C. for 2 h. The solvent was evaporated and the residue partitioned between DCM (50 mL) and water (50 mL). DCM layer separated and aqueous reextracted with DCM (3×50 mL). Combined organics were dried (Na$_2$SO$_4$) and evaporated. The residue was chromatographed on silica eluting with 5% MeOH/DCM, to give title compound (180 g, 80%) as a yellow solid which was triturated with diethylether to give a colourless solid, mp 239–241° C. $^1$H NMR (360 MHz, d$_6$-DMSO) δ2.60 (3H, s), 3.95 (3H, s), 5.69 (2H, s), 7.11 (1H, s),7.97 (1H, s), 9.53 (1H, s). Found: C, 40.28; H, 2.77; N, 28.45%. C$_{13}$H$_{11}$N$_8$O$_2$Br requires: C, 39.92; H, 2.83; N, 28.64%.

EXAMPLE 8

3-(Furan-2-yl)-7-(5-methylisoxazol-3-yl)-2-(1-methyl-1H-[1,2,4]triazol-5-ylmethoxy)pyrazolo[1,5-d][1,2,4]triazine A stirred mixture of 3-bromo-7-(5-methylisoxazol-3-yl)-2-(1-methyl-1H-[1,2,4]triazol-5-ylmethoxy)pyrazolo[1,5-d][1,2,4]triazine (Example 7) (80 mg, 0.20 mmol) in dioxan (10 mL) containing 2-tri-n-butylstannylfuran (146 mg, 0.41 mmol) was degassed with nitrogen for 20 min. Tetrakistriphenylphosphine palladium(0) (50 mg) and copper(I) iodide (5 mg) were added and the mixture heated at reflux for 8 h. Further stannane (146 mg, 0.41 mmol) and palladium catalyst (50 mg) were added and the mixture heated at reflux for 16 h. The solvent was evaporated and the residue purified on silica eluting with 5% MeOH/DCM to give a yellow solid (149 mg). The yellow solid was re-chromatographed on silica eluting with 5% MeOH/DCM to give a yellow solid (29 mg) which was triturated with diethylether to give the title compound (15 mg, 19%) as a yellow solid. mp 226–228° C. $^1$H NMR (360 MHz, CDCl$_3$) δ1.58 (9H, s), 2.61 (3H, s), 4.10 (3H, s), 5.78 (2H, s), 6.52–6.56 (1H, m), 6.75–6.79 (1H, m), 6.96 (1H, s), 7.57 (1H, s), 7.91 (1H, s), 9.71 (1H, s). Found: C, 52.68; h, 3.47; N, 28.64; C$_{17}$H$_{14}$N$_8$O$_3$.0.05(CH$_2$Cl$_2$).0.25(H$_2$O) requires: C, 52.90; H, 28.95%.

EXAMPLE 9

7-(5-Methylisoxazol-3-yl)-2-(1-methyl-1H-[1,2,4]triazol-5-ylmethoxy)-3-thiophen-3-ylpyrazolo[1,5-d][1,2,4]triazine A stirred mixture of the bromide (Example 7) (100 mg, 0.26 mmol), thiophene-3-boronic acid (49 mg, 0.38 mmol) and cesium carbonate (167 mg, 0.51 mmol) in dioxan (20 mL) was degassed by evaporating under high vacuum until cold then refilled with N$_2$ and allowed to thaw. This freeze/thaw procedure was repeated 3 times. Pd$_2$(dba)$_3$ (23 mg, 0.026 mmol) and tri-tert-butylphosphine (0.1M solution in dioxane) (0.6 mL, 0.06 mmol) were added and the degassing procedure repeated twice. The mixture was heated at 90° C. under a flow of nitrogen overnight. Further quantities of reagents were added at room temperature: thiophene-3-boronic acid (49 mg, 0.38 mmol), cesium carbonate (167 mg, 0.51 mmol), Pd$_2$(dba)$_3$ (23 mg, 0.026 mmol) and tri-tert-butylphosphine (0.6 mL, 0.06 mmol) followed by the degassing procedure 3 times. Heating was continued at 90° C. for a further 24 h. After cooling the mixture was filtered and the solid washed with EtOAc. The combined organic filtrates were washed with brine, dried (MgSO$_4$) and evaporated. The residue was purified using silica plug chromatography eluting with 1% MeOH/DCM to give the title compound (35 mg, 37%) as a yellow solid. MS (ES$^+$) 395 (M+1). $^1$H NMR (400 MHz, d$_6$-DMSO) δ2.61 (3H, s), 3.96

(3H, s), 5.74, (2H, s), 7.15 (1H, s), 7.69–7.71 (1H, m), 7.74–7.78 (1H, m), 7.96 (1H, s), 8.03–8.05 (1H, m), 9.85 (1H, s).

EXAMPLES 10 to 40

The following compounds of Formula IIA were prepared by analogous methods, as indicated in the following table:

| Ex. No. | $R^{1a}$ | Z' | X' | Method |
|---|---|---|---|---|
| 10 | t-butyl | 5-methylisoxazol-3-yl | 3-methyl-5-yl isoxazole | Ex. 2 |
| 11 | bromo | 5-methylisoxazol-3-yl | 1-methyl-4-yl-1,2,3-triazole | Ex. 7 |
| 12 | t-butyl | 5-methylisoxazol-3-yl | 3-methyl-1,2,4-oxadiazol-5-yl | Ex. 2 |
| 13 | t-butyl | 5-methylisoxazol-3-yl | 2-methylthiazol-4-yl | Ex. 2 |
| 14 | 2-furyl | 5-methylisoxazol-3-yl | 1-methyl-1,2,3-triazol-4-yl | Ex. 8 |
| 15 | bromo | isoxazol-3-yl | 1-methyl-1,2,4-triazol-3-yl | Ex. 7 |
| 16 | t-butyl | 5-methylisoxazol-3-yl | 1,5-dimethyl-1,2,3-triazol-4-yl | Ex. 2 |
| 17 | t-butyl | 5-methylisoxazol-3-yl | 1-methyl-1,2,3-triazol-4-yl | Ex. 2 |
| 18 | t-butyl | 5-methylisoxazol-3-yl | 3-methyl-5-oxo-1,2,4-triazol-yl | Ex. 2 |
| 19 | t-butyl | 5-methylisoxazol-3-yl | 6-trifluoromethylpyridin-3-yl | Ex. 2 |
| 20 | t-butyl | 5-methylisoxazol-3-yl | 1,2-dimethylimidazol-5-yl | Ex. 2 |
| 21 | t-butyl | 5-methylisoxazol-3-yl | thiazol-4-yl | Ex. 2 |
| 22 | t-butyl | 5-methylisoxazol-3-yl | 2-aminothiazol-4-yl | Ex. 2 |
| 23 | t-butyl | 5-methylisoxazol-3-yl | 5-amino-3-methyl-1,3,4-thiadiazol-yl | Ex. 2 |
| 24 | t-butyl | 5-methylisoxazol-3-yl | pyridazin-3-yl | Ex. 2 |

-continued

| Ex. No. | R¹ᵃ | Z' | X' | Method |
|---|---|---|---|---|
| 25 | t-butyl | 5-methylisoxazol-3-yl | 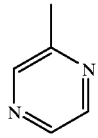 | Ex. 2 |
| 26 | t-butyl | 5-methylisoxazol-3-yl | 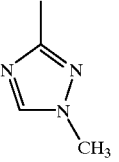 | Ex. 2 |
| 27 | t-butyl | 5-methylisoxazol-3-yl | 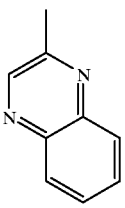 | Ex. 2 |
| 28 | t-butyl | isoxazol-3-yl | 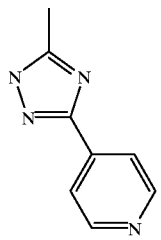 | Ex. 2 |
| 29 | t-butyl | isoxazol-3-yl | 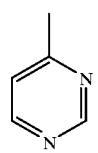 | Ex. 2 |
| 30 | t-butyl | isoxazol-3-yl | 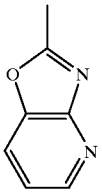 | Ex. 2 |
| 31 | t-butyl | isoxazol-3-yl | 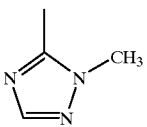 | Ex. 2 |
| 32 | t-butyl | 5-methylisoxazol-3-yl | 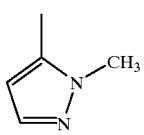 | Ex. 2 |
| 33 | 3-thienyl | isoxazol-3-yl | 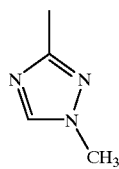 | Ex. 9 |
| 34 | t-butyl | 5-methylisoxazol-3-yl | 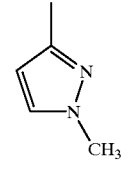 | Ex. 2 |
| 35 | t-butyl | 5-methylisoxazol-3-yl | 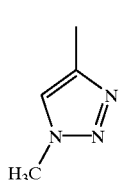 | Ex. 2 |
| 36 | t-butyl | 5-methylisoxazol-3-yl | 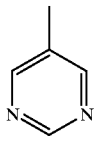 | Ex. 2 |
| 37 | t-butyl | 5-methylisoxazol-3-yl | 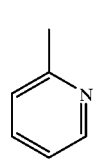 | Ex. 2 |
| 38 | t-butyl | 5-methylisoxazol-3-yl | 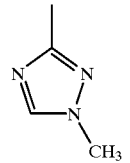 | Ex. 2 |
| 39 | bromo | 5-methylisoxazol-3-yl | 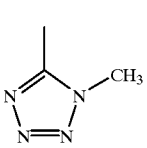 | Ex. 7 |
| 40 | 3-thienyl | 5-methylisoxazol-3-yl | 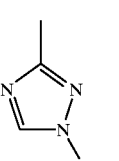 | Ex. 9 |

EXAMPLES 41 to 90

The following Examples were also made by analogous methods:

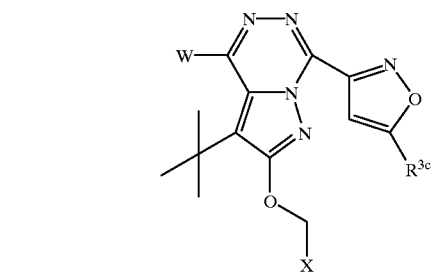

| Example | W | X | R3c |
|---|---|---|---|
| 41 | H | 2-methyl-1,2,4-triazol-3-yl | ethenyl |
| 42 | H | 2-methyl-1,2,4-triazol-3-yl | hydroxymethyl |
| 43 | H | 2-methyl-1,2,4-triazol-3-yl | 2-aminoethyl |
| 44 | H | 2-methyl-1,2,4-triazol-3-yl | aminomethyl |
| 45 | H | 5-(piperidin-1-ylmethyl)pyridin-2-yl | methyl |
| 46 | H | 2-(2-(azetidin-1-yl)ethyl)pyridin-5-yl | methyl |
| 47 | H | 2-(2-(morpholin-4-yl)ethyl)pyridin-5-yl | methyl |
| 48 | H | 2-(2-(piperazin-1-yl)ethyl)pyridin-5-yl | methyl |
| 49 | H | 2-(2-(piperidin-1-yl)ethyl)pyridin-5-yl | methyl |
| 50 | H | 2-(2-(N,N-dimethylamino)ethyl)pyridin-5-yl | methyl |
| 51 | H | 2-(2-aminoethyl)pyridin-5-yl | methyl |
| 52 | H | 2-(2-aminoethyl)-1,2,4-triazol-3-yl | methyl |
| 53 | H | 2-(morpholin-4-yl)methyl)pyridin-5-yl | methyl |
| 54 | H | 2-hydroxymethylpyridin-5-yl | methyl |
| 55 | H | 5-(4-methylpiperazin-1-ylmethyl | methyl |
| 56 | H | 5-(azetidin-1-ylmethyl)pyridin-2-yl | methyl |
| 57 | H | 5-(morpholin-4-ylmethyl)pyridin-2-yl | methyl |
| 58 | H | 4-hydroxymethyl-1-methyl-1,2,3-triazol-5-yl | methyl |
| 59 | H | 5-aminomethylpyridin-2-yl | methyl |
| 60 | H | 5-(N,N-dimethylaminomethyl | methyl |
| 61 | H | 1-methyl-3-hydroxymethyl-1,2,4-triazol-5-yl | methyl |
| 62 | H | 1-methyl-3-(morpholin-4-ylmethyl)-1,2,4-triazol-5-yl | methyl |
| 63 | H | 1-methyl-3-(piperidin-1-yl)-1,2,4-triazol-5-yl | methyl |
| 64 | H | 6-hydroxymethylpyridin-2-yl | methyl |
| 65 | H | 6-(2-(morpholin-4-yl)ethyl)pyridin-2-yl | methyl |
| 66 | H | 6-(2-piperazin-1-yl)ethyl)pyridin-2-yl | methyl |
| 67 | H | 5-trifluoromethylpyridin-2-yl | methyl |
| 68 | H | 6-(2-(piperidin-1-yl)ethyl)pyridin-2-yl | methyl |
| 69 | H | 1-methyl-3-(azetidin-1-ylmethyl)-1,2,4-triazol-5-yl | methyl |
| 70 | H | 1-methyl-3-((2,6-cis dimethylpiperidin-1-yl)methyl)-1,2,4-triazol-5-yl | methyl |

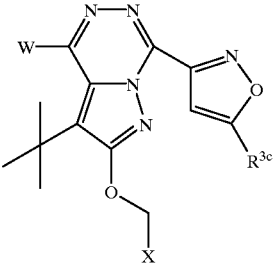

| Example | W | X | R3c |
|---|---|---|---|
| 71 | H | 2-methyl-3-hydroxymethyl-1,2,4-triazol-5-yl | methyl |
| 72 | H | 2-methyl-3-(N,N-dimethylaminomethyl)-1,2,4-triazol-5-yl | methyl |
| 73 | H | 2-methyl-3-(N,N-diethylaminomethyl)-1,2,4-triazol-5-yl | methyl |
| 74 | H | 1-methyl-3-(N,N-dimethylaminomethyl)-1,2,4-triazol-5-yl | methyl |
| 75 | H | 1-methyl-3-(N,N-diethylaminomethyl)-1,2,4-triazol-5-yl | methyl |
| 76 | H | 5-(N,N-diethylaminomethyl)pyridin-2-yl | methyl |
| 77 | H | 1-methyl-3-(2-(N,N-diethylamino)ethyl)-1,2,4-triazol-5-yl | methyl |
| 78 | H | 5-(N-ethylaminomethyl)pyridin-2-yl | methyl |
| 79 | H | 2-methyl-1,2,4-triazol-3-yl | 2-(tertiarybutoxycarbonylamino)ethyl |
| 80 | methyl | 2-methyl-1,2,4-triazol-3-yl | methyl |
| 81 | methyl | 5-hydroxymethylpyridin-2-yl | methyl |
| 82 | methyl | 5-(N,N-dimethylaminomethyl)pyridin-2-yl | methyl |
| 83 | methyl | 5-(N,N-diethylaminomethyl)pyridin-2-yl | methyl |
| 84 | H | 2-methyl-1,2,4-triazol-3-yl | iodo |
| 85 | H | 1,2,4-triazol-3-yl | methyl |
| 86 | H | 2-methyl-1,2,4-triazol-3-yl | 2-hydroxyethyl |
| 87 | H | 2-methyl-1,2,4-triazol-3-yl | 2-azetidin-1-yl ethyl |
| 88 | H | 2-methyl-1,2,4-triazol-3-yl | morpholin-4-yl ethyl |
| 89 R1 = ethenyl | H | 2-methyl-1,2,4-triazol-3-yl | methyl |
| 90 | H | LYX = CH2CON(CH3)2 | methyl |

What is claimed is:

1. A compound of formula I, or a salt thereof:

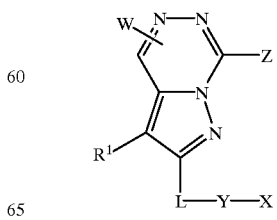

(I)

wherein

R¹ represents halogen; or $C_{1-6}$alkyl, $C_{3-7}$cycloalkyl, $C_{4-7}$cycloalkenyl, $C_{6-8}$bicycloalkyl, $C_{6-10}$aryl, azetidinyl, pyrrolidinyl, piperidinyl, piperazinyl, morpholinyl, thiomorpholinyl, heteroaryl or di($C_{1-6}$) alkylamino group, wherein said heteroaryl is defined as an aromatic ring containing either 6 atoms, 1, 2, or 3 of which are nitrogen, or 5 atoms, 1, 2 or 3 of which are independently chosen from oxygen, nitrogen, or sulphur but not more than one of which is oxygen or sulphur, and wherein any of which groups may be optionally substituted with one or more substituents selected from halogen, $R^3$, $OR^3$, $OC(O)R^3$, $NR^4R^5$, $NR^4R^5(C_{1-6})$alkyl, $NR^4R^5C(O)$, $NR^4R^5C(O)(C_{1-6})$alkyl, CN, cyano($C_{1-6}$)alkyl or $R^6$;

R³ represents $C_{1-6}$alkyl, $C_{2-6}$alkenyl, $C_{2-6}$alkynyl, $C_{3-6}$cycloalkyl, $C_{3-6}$cycloalkyl($C_{1-6}$) alkyl, cyano($C_{1-6}$)alkyl, hydroxy$C_{1-6}$alkyl and $R^3$ is optionally mono, di or trifluorinated;

R⁴ and R⁵ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with a nitrogen atom to which they are commonly attached, form azetidinyl, pyrrolidinyl, piperidinyl, piperazinyl, morpholinyl or thiomorpholinyl, optionally substituted by one or more $R^3$ groups;

R⁶ is $C_{6-10}$aryl, $C_{6-10}$aryl($C_{1-6}$)alkyl, heteroaryl or heteroaryl($C_{1-6}$)alkyl, where heteroaryl is defined as above, and $R^6$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy, $C_{2-4}$alkynyloxy groups each of which groups is unsubstituted or substituted by one, two or three halogen atoms;

L is O, S or $NR''$ where $R''$ is H, $C_{1-6}$alkyl or $C_{3-6}$cycloalkyl;

W is: $C_{1-6}$alkyl, $C_{2-6}$alkenyl or $C_{2-6}$alkynyl optionally substituted by one or more groups chosen from halogen, amino, nitro, cyano, hydroxy and halogen; hydrogen; amino; nitro; cyano; hydroxy; or halogen;

X is $NR^4R^5$; or X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene or pyridine ring and the heteroaromatic ring being optionally substituted by $R^x$ and/or $R^y$ and/or $R^z$, where $R^x$ is halogen, $R^3$, $OR^3$, $OC(O)R^3$, $C(O)OR^3$, $NR^4R^5$, $NR^4C(O)R^5$, OH, tri($C_{1-6}$alkyl)silyl$C_{1-6}$alkoxy$C_{1-4}$alkyl, CN or $R^6$, $R^y$ is halogen, $R^3$, $OR^3$, $OC(O)R^3$, $NR^4R^5$, $NR^4C(O)R^5$, $NR^4R^5(C_{1-6})$alkyl or CN and $R^z$ is $R^3$, $OR^3$ or $OC(O)R^3$, providing that when X is a pyridine derivative, the pyridine ring is optionally in the form of the N-oxide, and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

Y is optionally branched $C_{1-4}$alkylene optionally substituted by an oxo group or Y is a group $(CH_2)_jO$ wherein the oxygen atom is nearest the group X and j is 2, 3 or 4; and Z represents a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is also present, or a 6-membered heteroaromatic ring containing 2 ore 3 nitrogen atoms with the exception of pyrazine, any of which rings may be optionally substituted with one or more substituents selected from halogen, $R^3$, $OR^3$, $OC(O)R^3$, $NR^4R^5$, $NR^4R^5(C_{1-6})$alkyl, $NR^4R^5C(O)$, $NR^4R^5C(O)(C_{1-6})$alkyl, CN, cyano($C_{1-6}$)alkyl or $R^6$.

2. A compound of formula IIA, or a pharmaceutically acceptable salt thereof:

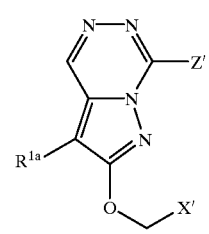

(IIA)

wherein $R^{1a}$ represents bromo, tert-butyl, 1,1-dimethylpropyl, phenyl, fluorophenyl, difluorophenyl, chlorophenyl, trifluoromethylphenyl, pyridinyl, furyl or thienyl;

X' represents phenyl, pyrazolyl, isoxazylyl, thiazolyl, imidazolyl, thiadiazolyl, benzimidazolyl, oxadiazolyl, triazolyl, tetrazolyl, pyridinyl, pyridazinyl, oxazolopyridinyl, pyrimidinyl, pyrazinyl, quinolinyl, isoquinolinyl or quinoxalinyl, any of which groups may be optionally substituted by one or more of $C_{1-6}$alkyl, amino, pyridyl, $CF_3$, aryl($C_{1-6}$)alkyl, pyridyl($C_{1-6}$) alkyl, halogen, cyano, cyano($C_{1-6}$)alkyl, hydroxymethyl, $C_{1-6}$alkoxy, $C_{3-6}$cycloalkyl($C_{1-6}$) alkoxy, hydroxy or the keto tautomer thereof, di($C_{1-6}$) alkylamino($C_{1-6}$)alkyl, amino($C_{1-6}$)alkyl, N-($C_{1-6}$) alkylpiperidinyl, pyrrolidinyl($C_{1-6}$)alkyl, piperazinyl ($C_{1-6}$)alkyl and morpholinyl($C_{1-6}$)alkyl; and Z' represents a 5-membered heteroaromatic ring containing one oxygen and one or two nitrogen ring atoms which is optionally substituted with one or two substituents independently $C_{1-6}$alkyl or $C_{1-6}$alkoxy.

3. A compound of formula IIB, or a pharmaceutically acceptable salt thereof:

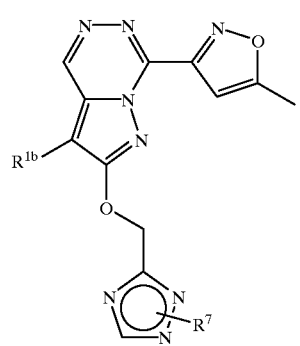

IIB wherein
- R$^{1b}$ represents bromo, thienyl, tert-butyl, phenyl or furyl; and
- R$^7$ represents hydrogen, methyl, ethyl, n-propyl or iso-propyl.

4. A compound which is:
- 7-(5-methylisoxazol-3-yl)-2-(1-methyl-1H-[1,2,4]triazol-3-ylmethoxy)-3-phenylpyrazolo[1,5-d][1,2,4]triazine;
- 3-tert-butyl-7-(5-methylisoxazol-3-yl)-2-(1-methyl-1H-[1,2,4]triazol-3-ylmethoxy)pyrazolo[1,5-d][1,2,4]triazine;
- 3-tert-butyl-7-(5-methylisoxazol-3-yl)-2-(1-methyl-1H-[1,2,4]triazol-5-ylmethoxy)pyrazolo[1,5-d][1,2,4]triazine;
- 3-tert-butyl-7-(5-methylisoxazol-3-yl)-2-(pyrid-2-ylmethoxy)pyrazolo[1,5-d][1,2,4]triazine;
- 3-tert-butyl-7-(5-methylisoxazol-3-yl)-2-(pyrid-3-ylmethoxy)pyrazolo[1,5-d][1,2,4]triazine; or
- 3-tert-butyl-7-(5-methylisoxazol-3-yl)-2-(pyrid-4-ylmethoxy)pyrazolo[1,5-d][1,2,4]triazine;

or a pharmaceutically acceptable salt thereof.

5. A pharmaceutical composition comprising a compound according to claim 1, or a pharmaceutically acceptable salt thereof, and a pharmaceutically acceptable excipient.

6. A method for enhancing cognition in a subject, such as a subject suffering from Alzheimer's Disease, which comprises administering a therapeutically effective amount of a compound of claim 1, or a pharmaceutically acceptable salt thereof to that subject.

7. A process for producing a compound of formula I as defined in claim 1 which comprises cyclising a compound of formula III:

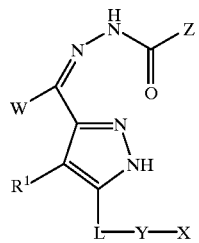

(III)

wherein R$^1$, L, W, X, Y and Z are as defined in claim 1.

8. A process for producing a compound according to claim 1 of formula I which comprises reacting a compound of formula IX with a compound of formula X:

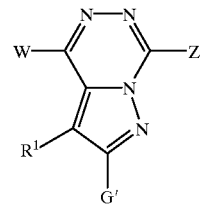

(IX)

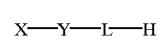

(X)

wherein R$^1$, L, W, X, Y and Z are as defined in claim 1, wherein W is not a halogen or halogen bearing moiety, and G' represents a suitable leaving group.

9. A process for producing a compound according to claim 1 of formula I which comprises reacting a compound of formula XII with a compound of formula XIII:

R$^1$—M  (XII)

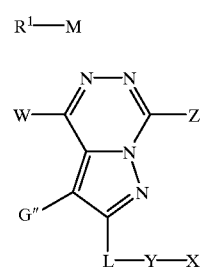

(XIII)

wherein R$^1$, L, W, X, Y and Z are as defined in claim 1, wherein W is not a halogen or halogen bearing moiety, G" represents a suitable leaving group, and M represents —B(OH)$_2$ or a cyclic ester thereof formed with an organic diol; and wherein the reaction is in the presence of a zero valent Pd catalyst.

* * * * *